April 22, 1952 C. McMULLEN Plant Pat. 1,084
SHASTA DAISY PLANT
Filed Feb. 13, 1951
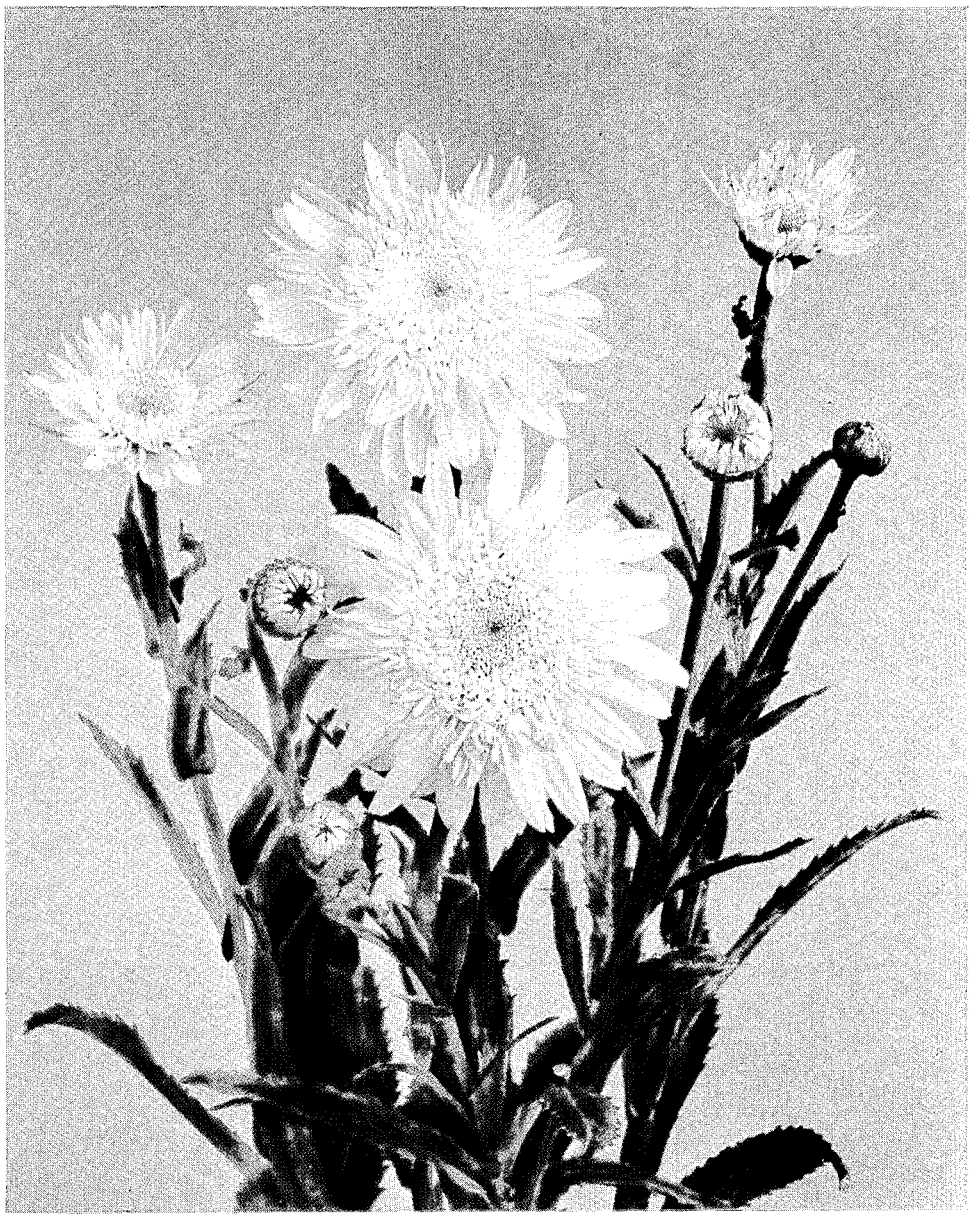
Inventor.
Colin McMullen
By: Robb & Robb
attorneys.

Patented Apr. 22, 1952

Plant Pat. 1,084

UNITED STATES PATENT OFFICE 1,084

SHASTA DAISY PLANT

Colin McMullen, Little Sutton, Wirral, England, assignor to Jackson & Perkins Company, Newark, N. Y., a corporation of New York Application February 13, 1951, Serial No. 210,680

1 Claim. (Cl. 47—60)

The present invention relates to a new and distinct variety of Shasta daisy plant, originating as a selected seedling of a cross of "Wirral Pride" (unpatented) × "Mount Everest" (unpatented).

This new variety is particularly characterized by its unique white flowers which are the large Anemone-flowered type of *Chrysanthemum maximum,* with outer petal rays and center cushion petals, obtained from the combination of the extremely large, prolific, 6-inch flowers of the "Mount Everest" variety and the Anemone-flowered, smaller cushion type "Wirral Pride."

In addition to the unusual size and different form above referred to, the new variety combines the distinctive features of vigorous growth and very prolific production of massive clumps of flowers to an extent which is unusual in the cushion type.

Due to the long-lastingness and excellent keeping qualities of the flowers of the new variety, and the fact that the flowers are borne on long, clean stems, the new variety is especially suited and desirable for cut-flower production.

Asexual reproduction of the new variety by division at Newark, New York, shows that the foregoing characteristics come true to form and are established and transmitted through succeeding propagations.

The accompanying drawing shows specimens of the flowers and foliage of the new variety in different stages of development.

The following is a detailed description of the new variety, with color terminology in accordance with Ridgway's Color Standards and Nomenclature:

Parentage: Selected seedling of cross "Wirral Pride" × "Mount Everest."

Type: A large Anemone-flowered type of *Chrysanthemum maximum.*

Locality where grown: Newark, New York.

Flower:

*Flowers borne.*—On long stems branching with new shoots and buds as the older flowers mature.

*Quantity of bloom.*—Very prolific.

*Continuity.*—Under Newark, New York, conditions, blooms with the regular *Chrysanthemum maximum* in June and July; also blooms again in August and September.

*Bud.*—Form—ball-shaped which opens gradually, starting with the white, Plate 53, of the ray petals.

Bloom:

*Type.*—Large Anemone-flowered type of *Chrysanthemum maximum* with outer petal rays and center cushion petals.

*Size.*—Attains size of 3½ to 4½ inches.

*Form.*—Consists of large cushion surrounded by three rows of petals of unequal length. Cushion consists of approximately 200 to 250 white, Plate 53, tubular florets. Cushion—the tubular florets begin opening from the outer perimeter and advance toward the center, leaving finally just a small showing of Light Cadmium, Plate 4.

*Petals or ray flowers.*—Quantity—about 50. Size—1¼ to 1⅜ inches long and extend about 1 inch beyond the outer edges of the cushion. Color—White, Plate 53. Lasting quality—exceptionally long on the plant and as a cut flower.

Plant:

*Stem.*—Stiff; 30 inches high; new branching starts about 6 to 8 inches from top.

*Foliage.*—Texture—is a typical *maximum* foliage of a Cress Green, Plate 31, with reverse Jade Green, Plate 31. Quantity—heavy foliage which persists throughout the summer.

Growth: Heavy clumps attaining height of 30 to 36 inches. Healthy and vigorous growth. Large clumps which produce 15 to 20 flowers each with stems of 24 to 30 inches.

I claim:

A new and distinct variety of Shasta daisy plant, characterized by its large size flowers of the Anemone-flowered type of *Chrysanthemum maximum,* said flowers being borne on long, clean stems and having long-lasting and excellent keeping qualities, and by its vigorous growth and very prolific production of massive clumps of white flowers of the cushion type, substantially as shown and described herein.

COLIN McMULLEN.

No references cited.